(12) United States Patent
Jackson

(10) Patent No.: US 7,513,905 B2
(45) Date of Patent: Apr. 7, 2009

(54) POLYAXIAL BONE SCREW

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 855 days.

(21) Appl. No.: 10/980,534

(22) Filed: Nov. 3, 2004

(65) Prior Publication Data
US 2006/0095038 A1 May 4, 2006

(51) Int. Cl.
A61B 17/70 (2006.01)
(52) U.S. Cl. .................. 606/266; 606/265; 606/267; 606/269; 606/305
(58) Field of Classification Search ......... 606/264–270, 606/300, 305–308; 411/283, 284
See application file for complete search history.

(56) References Cited

U.S. PATENT DOCUMENTS

| | | | |
|---|---|---|---|
| 3,456,704 A * | 7/1969 | Johnson | 411/284 |
| 5,261,912 A | 11/1993 | Frigg | |
| 5,312,404 A | 5/1994 | Asher et al. | |
| 5,360,431 A | 11/1994 | Puno et al. | |
| 5,429,639 A | 7/1995 | Judet | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,669,911 A | 9/1997 | Errico et al. | |
| 5,672,176 A | 9/1997 | Biedermann et al. | |
| 5,690,630 A | 11/1997 | Errico et al. | |
| 5,725,528 A | 3/1998 | Errico et al. | |
| 5,728,098 A | 3/1998 | Sherman et al. | |
| 5,733,286 A | 3/1998 | Errico et al. | |
| 5,782,833 A | 7/1998 | Haider | |
| 5,797,911 A | 8/1998 | Sherman et al. | |
| 5,800,435 A | 9/1998 | Errico et al. | |
| 5,817,094 A | 10/1998 | Errico et al. | |
| 5,879,350 A | 3/1999 | Sherman et al. | |
| 5,885,286 A | 3/1999 | Sherman et al. | |

(Continued)

FOREIGN PATENT DOCUMENTS

DE 9202745.8 4/1992

(Continued)

OTHER PUBLICATIONS

*EBI Omega 21* Brochure, EBI Spine Systems, pub. 1999.

(Continued)

*Primary Examiner*—Eduardo C Robert
*Assistant Examiner*—Andrew Yang
(74) *Attorney, Agent, or Firm*—John C. McMahon

(57) ABSTRACT

A polyaxial bone screw assembly includes a threaded shank body having an upper capture structure, a head, a retaining ring and a nut. The external capture structure surface includes a threaded portion and a smooth portion; the smooth portion for slidably mating with the retaining ring and the threaded portion for rotatable attachment to the nut within a cavity of the head. The nut fixes the retaining ring to the shank and also provides a tool engagement formation for driving the shank body into bone.

31 Claims, 4 Drawing Sheets

U.S. PATENT DOCUMENTS

| | | | |
|---|---|---|---|
| 5,891,145 A | 4/1999 | Morrison et al. | |
| 5,964,760 A | 10/1999 | Richelsoph | |
| 6,010,503 A | 1/2000 | Richelsoph et al. | |
| 6,019,759 A | 2/2000 | Rogozinski | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,132,432 A | 10/2000 | Richelsoph | |
| 6,146,383 A | 11/2000 | Studer et al. | |
| 6,187,005 B1 | 2/2001 | Brace et al. | |
| RE37,161 E | 5/2001 | Michelson et al. | |
| 6,224,596 B1 | 5/2001 | Jackson | |
| 6,248,105 B1 | 6/2001 | Schlapfer et al. | |
| 6,254,602 B1 | 7/2001 | Justis | |
| 6,273,888 B1 | 8/2001 | Justis | |
| 6,280,442 B1 | 8/2001 | Barker et al. | |
| 6,287,308 B1 | 9/2001 | Betz et al. | |
| 6,287,311 B1 | 9/2001 | Sherman et al. | |
| 6,302,888 B1 | 10/2001 | Mellinger et al. | |
| 6,368,321 B1 | 4/2002 | Jackson | |
| 6,471,705 B1 | 10/2002 | Biedermann et al. | |
| 6,485,494 B1 | 11/2002 | Haider | |
| 6,488,681 B2 | 12/2002 | Martin et al. | |
| 6,554,834 B1 | 4/2003 | Crozet et al. | |
| 6,565,565 B1 | 5/2003 | Yuan et al. | |
| 6,565,567 B1 | 5/2003 | Haider | |
| 6,695,843 B2 | 2/2004 | Biedermann et al. | |
| 6,716,214 B1 | 4/2004 | Jackson | |
| 2001/0001119 A1 | 5/2001 | Lombardo | |
| 2002/0143341 A1 | 10/2002 | Biedermann et al. | |
| 2004/0172022 A1* | 9/2004 | Landry et al. | 606/61 |
| 2005/0143737 A1* | 6/2005 | Pafford et al. | 606/61 |

FOREIGN PATENT DOCUMENTS

| | | |
|---|---|---|
| DE | 19507141 | 9/1996 |
| EP | 1121902 | 8/2001 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek.
*Contour Spinal System* Brochure, Ortho Development.
*Xia Spinal System* Brochure, Stryker Howmedica Osteonics.
*The Rod Plate System* Brochure, Stryker Howmedica Osteonics, pub. Oct. 1999.
*Silhouette Spinal Fixation System* Brochure, Sulzer Medica Spine-Tech.
*SDRS Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation Advertisement*, Blackstone Medical Inc.
*The Moss Miami 6.0mm System* Advertisement, author unknown.

\* cited by examiner

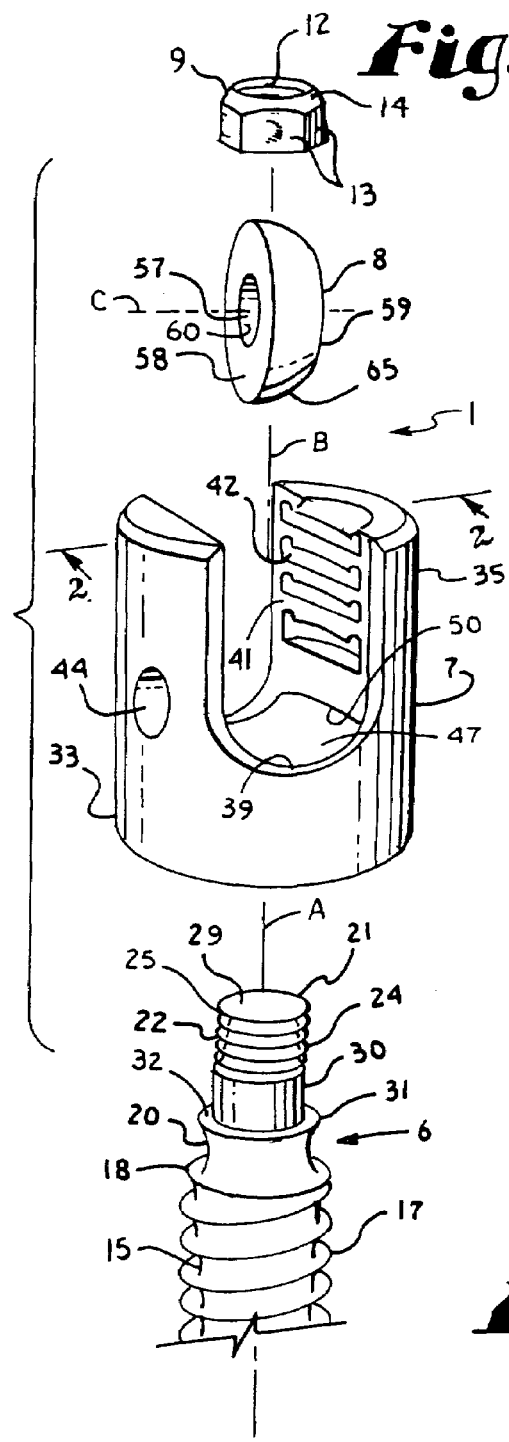
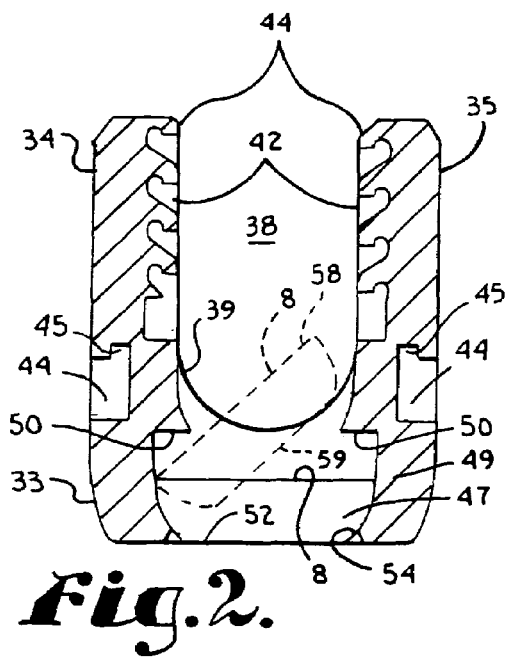
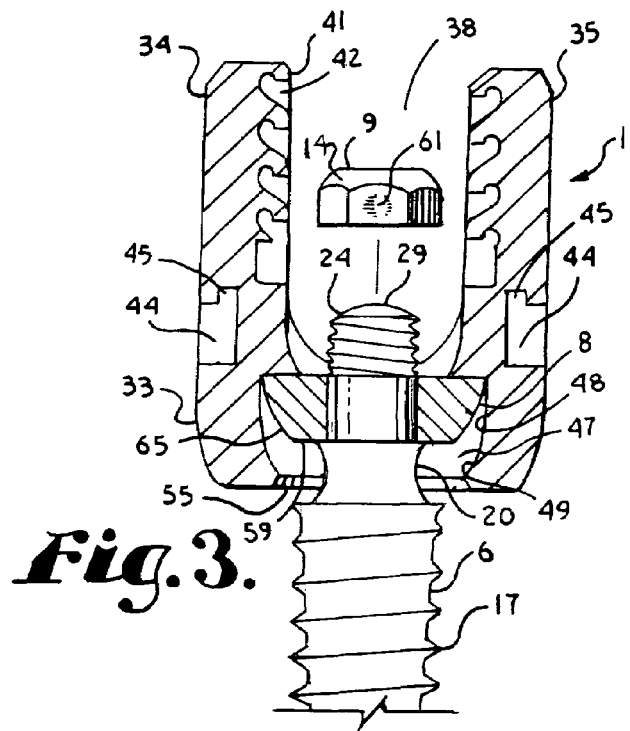
Fig.1.
Fig.2.
Fig.3.

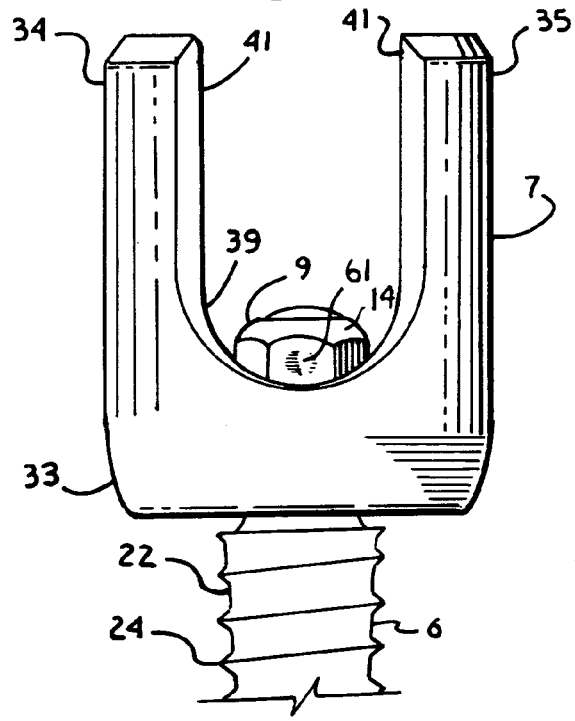
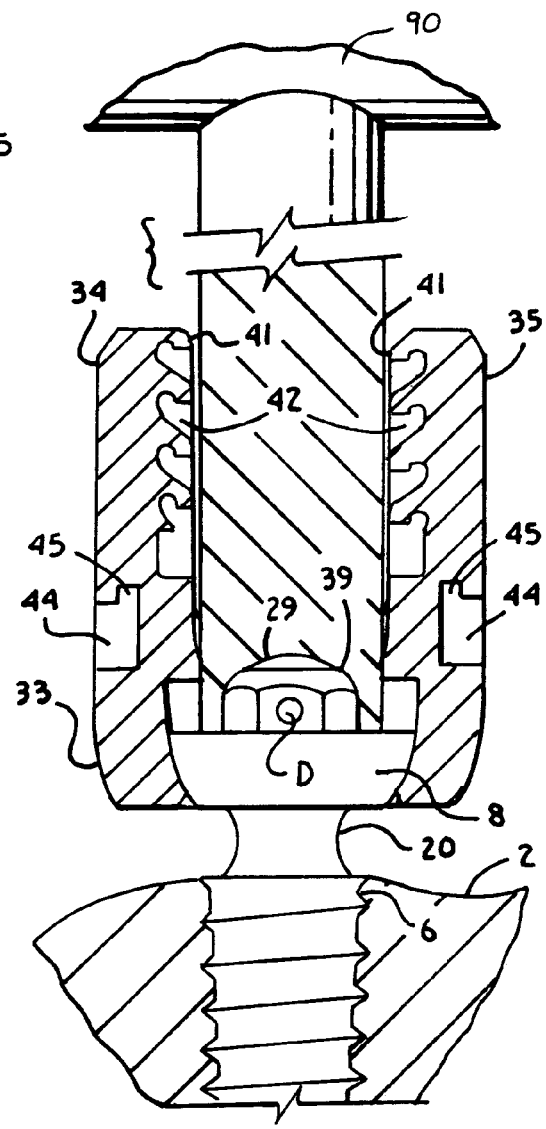
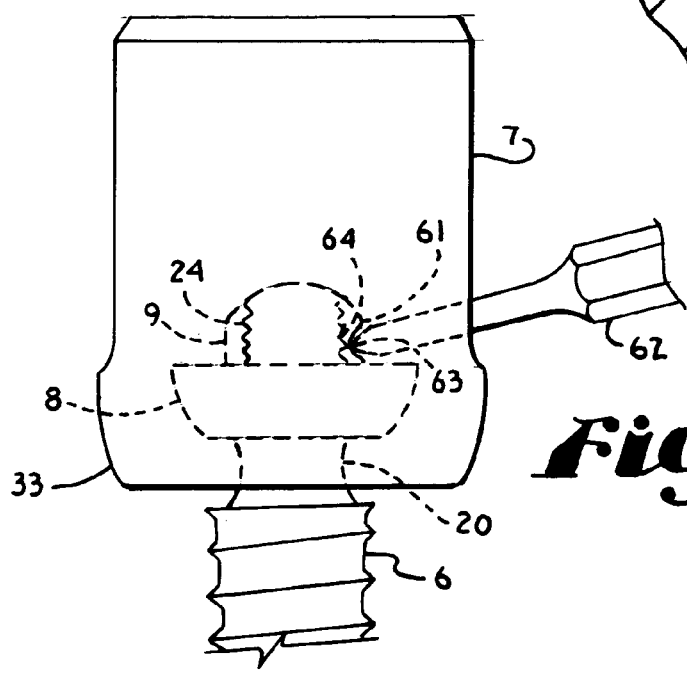

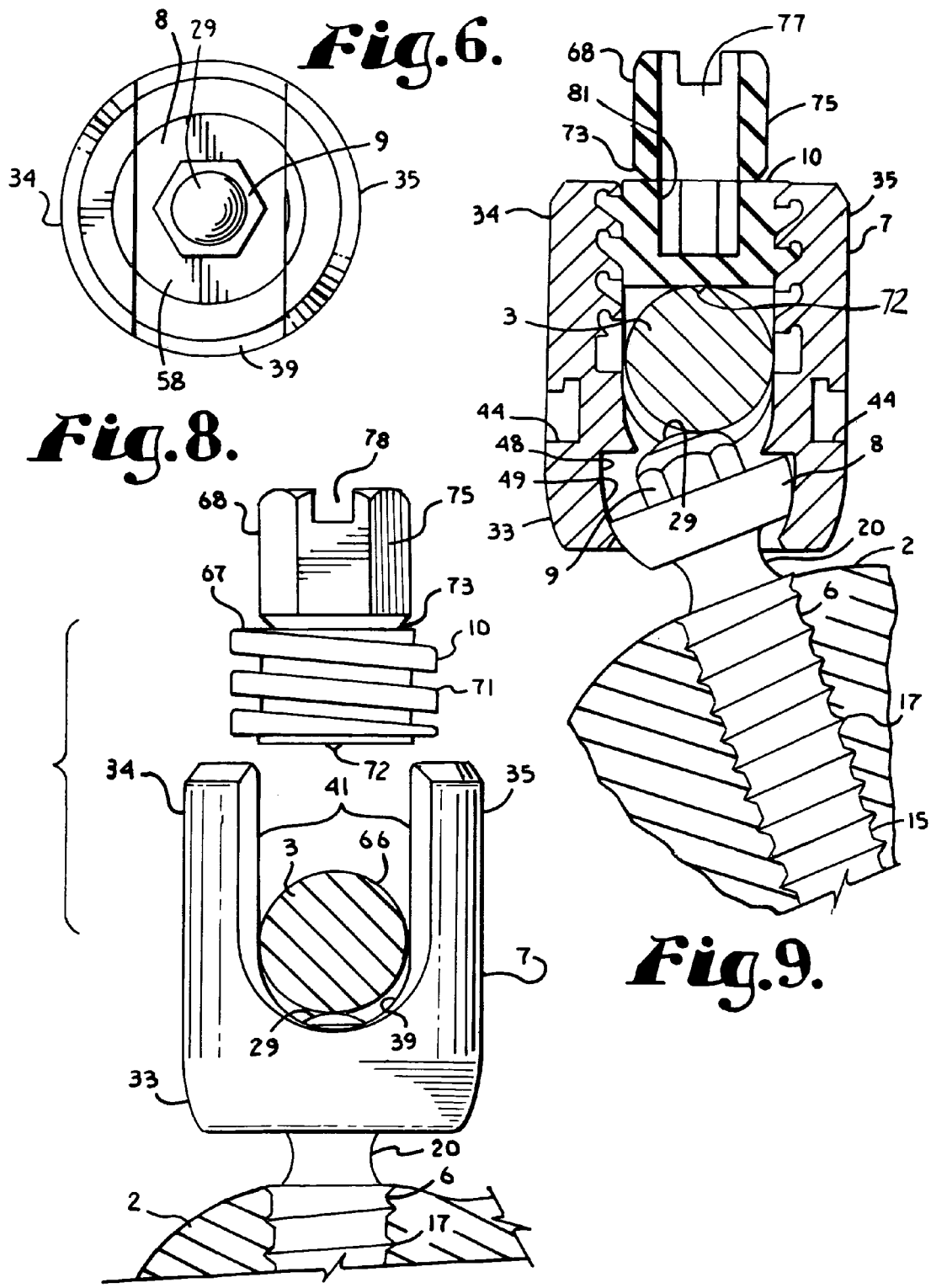

POLYAXIAL BONE SCREW

BACKGROUND OF THE INVENTION

The present invention is directed to polyaxial bone screws for use in bone surgery, particularly spinal surgery. Such screws have a head that can swivel about a shank of the bone screw, allowing the head to be positioned in any of a number of angular configurations relative to the shank.

Many spinal surgery procedures require securing various implants to bone and especially to vertebrae along the spine. For example, elongate rods are often required that extend along the spine to provide support to vertebrae that have been damaged or weakened due to injury, disease or the like. Such rods are often supported by certain vertebrae and support other vertebrae. The most common mechanism for joining the rod to the spine is to implant bone screws into certain vertebrae which then in turn support the rod or are supported by the rod. Bone screws of this type may have a fixed head relative to a shank thereof. In the fixed bone screws, the head cannot be moved relative to the shank and the rod must be favorably positioned in order for it to be placed within the head. This is sometimes very difficult or impossible to do.

Polyaxial bone screws allow swivelling of the head relative to the shank to accommodate placement of the rod and are most commonly used. In particular, a polyaxial bone screw allows rotation of the head about the shank until a desired rotational position is achieved for the head relative to the shank, after which the rod can be laid or urged into a channel in the head. The position of the head is eventually locked with respect to movement relative to the shank by friction produced by combination of parts or other means before or after the rod is inserted in the head. Often, the rod is retained in the head and/or pressure is exerted against the rod by a closure top, plug or the like to capture the rod in the head of the screw.

Because such implants are for placement within the human body, it is desirable for the implant to have as little effect on the body as possible. Consequently, it is quite desirable for the implants to have a relatively small profile both in height and width. It is also desirable that the implants be lightweight.

One undesirable attribute of some of the swivel-head implants is the need for a multitude of components that may loosen or even disassemble within the body. It is most undesirable for components to be free to move around in the body after the completion of surgery. Loosening of components relative to each other may result in related undesirable movement of the bone or vertebra that the implant was intended to stabilize. Consequently, it is desirable for there to be a lightweight, low profile polyaxial bone screw which assembles in such a manner that subsequent pieces lock preceding pieces within the overall structure, so that there is less likelihood that the various pieces of the structure will undesirably disassemble.

SUMMARY OF THE INVENTION

A polyaxial bone screw assembly of the present invention includes a shank having a body for fixation to a bone. Integral with the shank and extending axially upwardly and outwardly therefrom is a capture structure. The capture structure has a radially projecting outer surface that is substantially cylindrical and that further includes a helically wound structure, such as a thread and an adjacent smooth surfaced portion. The upper end of the shank is convexly curved.

The bone screw assembly further includes a head having a top portion and a base. The top portion is open and has a channel. The base also is upwardly open and includes an inner seating surface partially defining a cavity and has a lower aperture or opening. The channel of the top portion communicates with the cavity, which in turn communicates with an exterior of the base of the head through the base opening. The base opening is sized and shaped to receive the capture structure of the shank into the head cavity.

The bone screw assembly further includes a closed retaining ring that has an internal surface defining a bore, the internal surface sized and shaped to mate with the smooth surface portion of the capture structure when the retaining ring and the capture structure are coaxially aligned within the head cavity and the capture structure is received in the retaining ring bore.

The external surface of the retaining ring is configured to be in slidable mating engagement with the surface defining the cavity of the head. Preferably, the retaining ring external surface and the mating head inner surface are substantially spherical. However, it is noted that the mating surfaces may be of another shape, such as conical or tapered, especially for the head cavity inner surface. The cooperating shapes of the retaining ring external surface and the head inner surface enable selective angular positioning of the shank body with respect to the head.

The retaining ring is fixed to the capture structure with a threaded fastener or nut. The nut includes a faceted outer surface and an internal surface having a helically wound structure configured for mating with the outer helically wound structure of the capture structure. The nut is top loaded into the head, axially aligned with the shank and attached retaining ring, and then rotated until the retaining ring is captured between the nut and the shank body. Preferably, the shank capture structure includes an annular seating surface that abuts against the retaining ring at one side thereof when the nut contacts and presses against the retaining ring at another side thereof.

Also, according to the invention, preferably at least one facet of the nut has a weakened area compressible by an outside pressing force directed at the weakened area, such as a set tool. When pressure is placed on the weakened area, pressure also is placed on the helically wound structure of the capture structure and the helically wound structure of the nut. At least one or both of these helically wound structures are deformed by the pressure that is placed on the weakened area of the nut, interlocking the helically wound structures, and thus locking the retaining ring in a preferred position between the nut and the shank body.

The nut faceted outer surface also provides a tool engagement formation extending from the capture structure for non-slip engagement by a tool for driving the shank into bone and may also be cooperatively used for attaching the nut and retaining ring to the capture structure. When utilized for driving the shank into bone, a top surface of the retaining ring disposed adjacent to the nut faceted outer surface also provides an additional gripping surface for a driving tool.

Preferably, the head cavity is partially defined by an upper shoulder portion having planar surface portions disposed perpendicular to an axis of rotation of the head. An advantage of the upper shoulder is that the retaining ring may be pressed against the upper shoulder during assembly of the nut on the capture structure, keeping the retaining ring seated evenly upon the capture structure during such assembly.

A polyaxial bone screw assembly method according to the invention includes inserting a closed retaining ring into a head cavity, inserting a capture structure of a bone screw shank through a shank receiving opening of the head and into a cavity thereof and then into the retaining ring; and attaching the capture structure to the retaining ring within the head utilizing a nut. A method according to the invention further includes driving the shank body into bone by rotating the shank body with a tool engaged with the nut. Further assembly steps according to the invention include inserting a rod into the channel; and biasing the rod against a top of the bone screw shank capture structure by rotatably inserting a closure member structure within or onto a mating structure of the head.

OBJECTS AND ADVANTAGES OF THE INVENTION

Therefore, it is an object of the present invention to overcome one or more of the problems with polyaxial bone screw assemblies described above. A further object of the invention is to provide apparatus and methods directed to a shank that uploads into a cavity in a head of the screw and that utilizes a retaining structure that is downloaded into the cavity. Another object of the invention is to provide a lightweight, low profile polyaxial bone screw that assembles in such a manner that the components cooperate to guard against disassembly after implantation. Another object of the invention is to provide bone screw components that do not require overly complicated fasteners or complicated methods of fastening within the bone screw head. Another object of the invention is to provide a polyaxial bone screw with features that present frictional or gripping surfaces for bone implantation tools and may be readily and securely fastened to each other as well as to the bone. A further object of the invention is to provide a polyaxial bone screw that is easily removable from the bone, if desired, as a single unit. Furthermore, it is an object of the invention to provide apparatus and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention, including a shank, a head, a retaining ring and a nut.

FIG. 2 is an enlarged cross-sectional view of the head, taken along the line 2-2 of FIG. 1, illustrating the retaining ring being inserted into the head.

FIG. 3 is an enlarged cross-sectional view of the head similar to FIG. 2, shown with a retaining ring of FIG. 1, shown in cross-section, disposed in the head and seated on the shank upper end, and also shown with a nut of FIG. 1 prior to the nut being rotatably inserted onto the shank upper end.

FIG. 4 is an enlarged side elevational view of the bone screw of FIG. 1, shown assembled.

FIG. 5 is an enlarged front elevational and fragmentary view of the bone screw of FIG. 4, illustrating a set tool with a tool tip pressing against the nut and deforming a thread of the shank.

FIG. 6 an enlarged top plan of the bone screw of FIG. 4.

FIG. 7 is an enlarged, cross-sectional view of the head of FIG. 2, shown assembled with the shank, retaining ring and nut, and illustrating an installment tool being used to drive the bone screw shank into the vertebra.

FIG. 8 an enlarged side elevational and partially exploded view of the installed bone screw of FIG. 7, showing the head with a rod received in the U-shaped channel and prior to a closure top being rotatably inserted into the head.

FIG. 9 is a cross-sectional view of the vertebra, head, rod and closure top of FIG. 8, showing the shank implanted in the vertebra and with the bone screw assembly in a completely assembled and operational configuration with the closure top installed and the shank locked in an angled orientation with respect to the head.

DETAILED DESCRIPTION OF THE INVENTION

Figure 10:
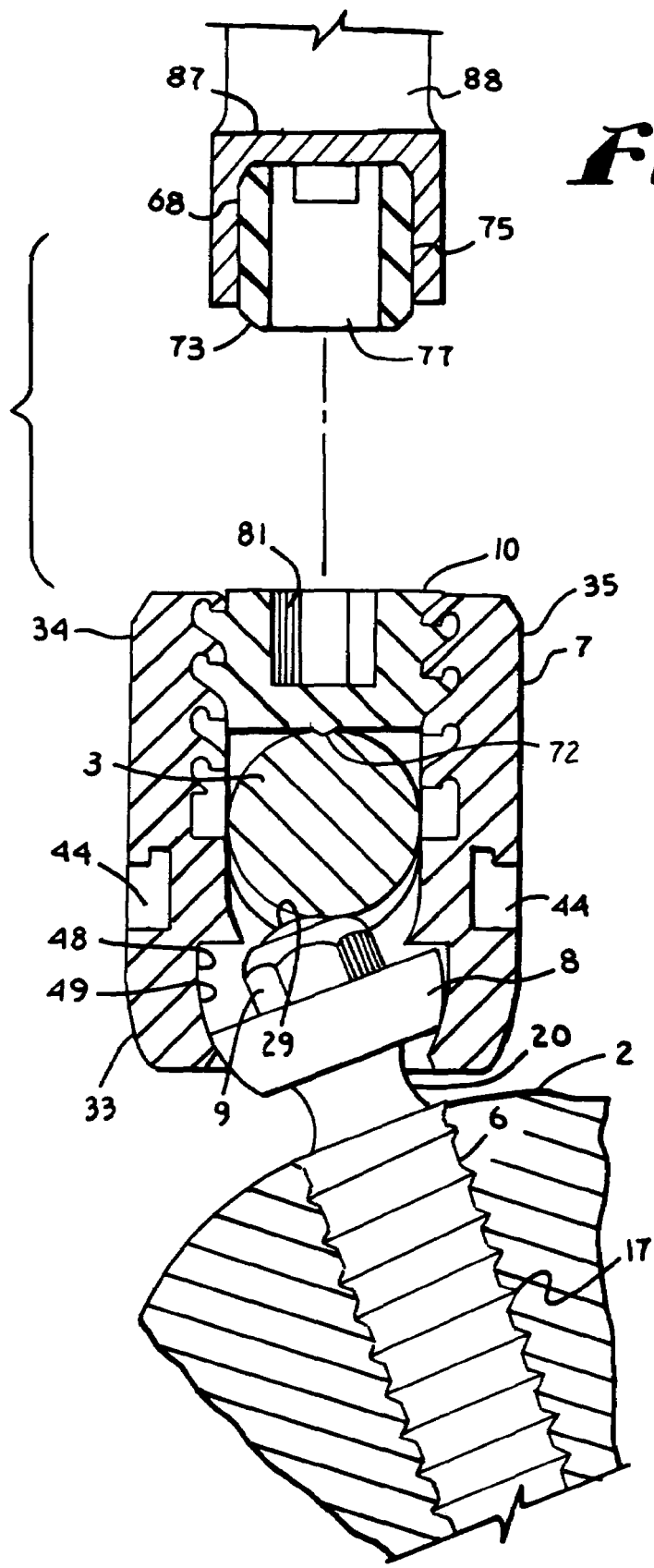
FIG. 10 is a cross-sectional view similar to FIG. 9, showing a break-off head being removed from the closure top by a socket head of a torquing tool.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally represents a polyaxial bone screw apparatus or assembly according to the present invention, operably utilized by implantation into a vertebra 2 and in conjunction with a longitudinal member or rod 3 so as to secure the rod 3 in a fixed position relative to the vertebra 2.

With reference to FIGS. 1 and 8, the bone screw assembly 1 includes a shank 6, a head 7, a retaining structure or ring 8, a fastener or nut 9 and a closure structure or top 10. The nut 9 includes an inner raised helical rib or thread 12, an external hexagonally faceted surface 13 and a slightly radiused or curved top surface 14. The shank 6 is elongate and has a lower body 15, as illustrated in FIG. 9, ending in a tip (not shown). The shank body 15 has a helically wound bone implantable thread 17 extending from near the tip (not shown) to near a top 18 of the body 15 and extending radially outward therefrom. During use, the body 15 utilizing the thread 17 is implanted into the vertebra 2, as is shown in FIG. 9. The shank 6 has an elongate axis of rotation A. It is noted that the reference to the words top and bottom, upper and lower, and the like, as used herein refers to the alignment shown in the various drawings, as well as the normal connotations applied to such devices, and is not intended to restrict positioning of the assembly 1 in actual use.

Extending axially outward and upward from the shank body 15 is a neck region 20, substantially hyperboloid in configuration, having a minimum radius smaller than a radius at the top 18 of the body 15. Further extending axially and outwardly from the neck 20 is a capture structure 21 providing a connective or capture portion of the shank 6. The neck region 20 provides a space between the capture structure 21 and the shank body 15, operably also spaced from the bone or vertebra 2 for adjoining with the head 7. The capture structure 21 has a radially outer cylindrical surface 22 with an external helically wound guide and advancement structure illustrated as a rib or thread 24. The thread 24 is located near an upper end 25 of the shank 6 and is sized and shaped to receive the threaded nut 9. Although a simple raised helical rib or thread 24 is shown in the drawings, it is foreseen that other structures including other types of threads, such as buttress and reverse angle threads, and non threads, such as helically wound flanges with interlocking surfaces, may be used in alternative embodiments of the present invention.

Also located at the shank upper end 25 is a centrally located, axially extending and upwardly directed projection or dome 29 that is centrally radiused so as to have a first radius. The projection 29 is preferably curved or dome-shaped as shown in the drawings, for positive engagement with the rod 3, when the bone screw assembly 1 is assembled, as shown in FIG. 10, and in any alignment of the shank 6 relative to the head 7. In certain embodiments, the surface 29 is smooth. While not required in accordance with practice of the invention, the domed surface 29 may be scored or knurled to further increase frictional engagement between the dome 29 and the rod 3. Also as illustrated in FIG. 10, preferably the nut top surface 14 has the same or similar first radius as the dome 29 to provide a continuous, positive engagement with the rod 3 at any alignment of the shank 6 with respect to the head 7.

Disposed between the neck 20 and the threads 24 of the capture structure 21 is a smooth cylindrical surface 30 terminating at a lower shoulder 31. The shoulder 31 is disposed adjacent to the neck 20 and includes an annular seating surface 32 oriented perpendicular to the axis of rotation A. The surface 32 extends outwardly radially from the cylindrical surface 30. The shoulder 31 divides the smooth cylindrical surface 30 from the neck 20 of the shank 6. The cylindrical surface 30 has a reduced inner radius relative to a maximum radius of the neck 20 adjacent the shoulder 31. The cylindrical surface 30 is sized and shaped to slidingly mate with the retaining ring 8 and centrally position the retaining ring 8 in alignment with the shank axis A and also generally centrally within the head 7, as will be discussed more fully below.

The head 7 has an outer profile that is substantially cylindrical in shape, as shown in FIG. 1. However, the head 7 is not a solid cylinder, but rather includes inner openings, a cavity and a channel described more fully hereafter, and being substantially symmetrical with respect to an axis of rotation B of the head 7. The head 7 includes a base 33 integral with a pair of upstanding arms 34 and 35. The arms 34 and 35 form a U-shaped channel 38 therebetween, defined in part by a lower seat 39 having substantially the same radius as the rod 3 for operably snugly receiving the rod 3. Each of the arms 34 and 35 has an interior surface 41 that includes a partial, helically wound guide and advancement structure 42. In the illustrated embodiment, the guide and advancement structure 42 is a partial helically wound flangeform configured to mate under rotation with a similar structure on the closure top 10, as described more fully below. However, it is foreseen that the guide and advancement structure 42 could alternatively be a V-shaped thread, a buttress thread, a reverse angle thread or other thread like or non-thread like helically wound advancement structure for operably guiding under rotation and advancing the closure top 10 between the arms 34 and 35.

Tool engaging apertures 44 are formed on outer surfaces of the arms 34 and 35 for holding the head 7 during assembly and also during the implantation of the shank body 15 into the vertebra 2. The apertures 44 are disposed opposite one another and each include respective upwardly projecting, hidden inner recesses 45. A holding tool (not shown) is sized and shaped to have structure to mate with and to be received in the apertures 44 and locked into place by pulling the holding tool slightly axially upward relative to the base 33 and toward the channel 38 formed by the arms 34 and 35 with a portion of the holding tool extending into the recesses 45. The holding tool and respective apertures 44 may be configured for a flexible twist or snap on/snap off engagement wherein the holding tool has legs which splay outwardly to position the tool for engagement in the apertures 44. It is noted that the apertures 44 and the cooperating holding tool may be configured to be of a variety of sizes and locations along any of the surfaces of the arms 34 and 35.

A chamber or cavity 47 is located within the head base 33 that opens upwardly into the U-shaped channel 38. The cavity 47 is defined in part by a partially spherically shaped inner surface 48, at least a portion of which forms a partial internal hemispherical seat 49. The surface or seat 49 is sized and shaped for mating with the retaining ring 8, as described more fully below. The hemispherically shaped surface 49 has a second radius associated therewith. At the opening into the U-shaped channel 38, the cavity 47 is defined in part by a discontinuous shoulder or upper coplanar seat 50 disposed on each of the arms 34 and 35 extending radially and substantially perpendicular to the axis B, as illustrated in FIG. 2.

At a bottom of the base 33, the cavity 47 communicates with a substantially circular bore 52 opening to an exterior of the base 33. The bore 52 is coaxial with the rotational axis B of the head 7. The bore 52 is defined at least in part by a restrictive neck 54 that has a radius that is smaller than an outer radius of the ring 8, as will be discussed further below, so as to form a restrictive constriction at the location of the neck 54 relative to the retaining ring 8 to prevent the ring 8 from passing between the cavity 47 and the lower exterior of the base 33 of the head 7. However, it is foreseen that the retaining ring 8 could be compressible and thus loadable through the neck 54 and then allowed to expand and fully seat in the spherical seating surface 49. A bevel 55 extends between the neck 54 and the bottom exterior of the base 33.

The retaining ring 8 is used to retain the capture structure 21 of the shank 6 within the head 7. The retaining ring 8, best illustrated by FIGS. 1-3, has an operational central axis that is the same as the elongate axis A associated with the shank 6, but when the retaining ring 8 is separated from the shank 6, the axis of rotation is identified as axis C, as shown in FIG. 1. The ring 8 has a central bore 57 disposed along the central axis C, with the central bore 57 passing entirely through the retaining ring 8 from a top surface 58 to a bottom surface 59 thereof. The bore 57 is sized and shaped so that the ring 8 fits snugly but slidably over the shank capture structure 21 and outer cylindrical surface 30 in such a manner as to allow sliding axial movement therebetween under certain conditions, as described below. A surface 60 defining the bore 57 is smooth and has a radius configured to be only slightly larger than an outer radius of the cylindrical surface 30, providing for slidable mating engagement between the surface 60 and the surface 30. As will be described subsequently in more detail, the shank capture structure 21 is uploadable into the head 7, and through the ring 8 that is already disposed in the head 7, by axially sliding the capture structure 21 through the ring central bore 57 until the ring bottom surface 59 is seated on the annular surface 32 of the shank 6, as illustrated in FIG. 3.

To secure the retaining ring 8 within the head 7, the inner thread 12 of the nut 9 is mated to the outer thread 24 of the capture structure 21. Similar to the thread 24, although a simple raised helical rib or thread 12 is shown in the drawings, it is foreseen that other structures including other types of threads, such as buttress and reverse angle threads, and non threads, such as helically wound flanges with interlocking surfaces, may be used in alternative embodiments of the present invention.

The mating of the nut inner thread 12 and the capture end outer thread 24 is aided by the shoulder 50 of the head 7. As illustrated in FIG. 3, after receiving the retaining ring 8 thereon, the shank 6 may be moved upwardly, until the top surface 58 of the ring 8 abuts the flat shoulder 50 at each of the arms 34 and 35, providing a relatively stable position for receiving the nut 9. The nut 9 is then top loaded into the head 7 through the channel 38, placed in axial alignment with the shank 6, lowered onto the shank capture structure 21, and rotated in a clock-wise direction when viewed from above. The nut 9 may be installed with a socket-type tool, similar to the tool 90 shown in FIG. 7 utilized for implanting the assembly 1 in a vertebra 2. The socket-type tool mates with the external faceted hexagonal surface 13, and is rotated and driven downward until the bottom surface 59 of the ring 8 abuts the annular surface 32 of the lower shoulder 31 and is frictionally fixed thereto. When the ring 8 abuts the annular surface 32, the dome 29 protrudes axially above the nut 9 with the nut top surface 14 disposed contiguous to the dome 29. The dome 29 and the top surface 14 preferably forming a continuous curved perimeter, the surface 14 extending the first radius of the dome 29, as illustrated in FIG. 4.

To further ensure frictional engagement between the nut 9 and the capture structure 21 of the shank 6, the nut 9 includes one or more weakened areas 61 located along the faceted surface 13 thereof. As shown in FIG. 5, a set tool 62 having a tip 63 passes between the upstanding arms 34 and 35 of the head 7 and pushes against the nut 9 at the weakened area 61, the tip 63 indenting the area 61, forming an indentation or deformation D on the nut surface, and also pressing against the thread 12 and/or the thread 24, creating or causing a deformed thread portion or portions 64, interlocking the threads 12 and 24, which in turn lodges the ring 8 in a fixed position with respect to the shank 6. The deformed thread portion or portions 64 prevent counter-clockwise rotation of the nut 9 with respect to the shank capture structure 21, and thus prevents the nut 9 and the ring 8 from migrating up and off the shank upper end 25 and into the channel 38, away from the desired position within the head 7.

The ring 8 has a radially outer partially hemispherically shaped surface 65 sized and shaped to slidingly mate with the partially hemispherically shaped seating surface 49. The surface 65 has a third radius approximately equal to the second radius associated with the seating surface 49. The third radius of the ring surface 65 is substantially larger than the first radius associated with the dome 29 and also substantially larger than an inner radius of the neck 54. Although not required, it is foreseen that the outer partially spherically shaped surface 65 may be a high friction surface such as a knurled surface or the like.

Preferably, the retaining ring 8 is constructed of a metal or other material having sufficient resilience and elasticity so as to allow the ring 8 to radially expand slightly outward by downward pressure of the nut 9 on the top surface 58 and under pressure from structure above, as will be discussed further below. This produces a slight outward radial expansion in the ring 8 at the shoulder 31 of the shank 6.

The longitudinal member or elongate rod 3 can be any of many different types of implants utilized in reconstructive spinal surgery and the like, but is normally a cylindrical elongate structure having a smooth, cylindrical surface 66 of uniform diameter. The rod 3 is preferably sized and shaped to snugly seat near the bottom of the U-shaped channel 38 at the lower seat 39 and, during normal operation, will be positioned slightly above a bottom of the channel 38. In particular, the rod 3 normally engages the shank dome 29, as illustrated in FIGS. 8-10, and urges against the dome 29 and, consequently, downwardly against the shank 6 when the assembly 1 is fully assembled. For this to occur, the shank domed surface 29 must extend at least slightly into the space of the channel 38 when the retaining ring 8 is snugly seated in the lower seat 49 of the head cavity 47. The shank 6 and retaining ring 8 are thereby locked or held in position relative to the head 7 by the rod 3 firmly pushing downward on the shank domed surface 29. At certain degrees of inclination of the shank 6 with respect to the head 7, the rod 3 may push downward on both the domed surface 29 and a portion of the nut top surface 14.

With reference to FIGS. 8, 9 and 10, the closure structure or closure top 10 can be any of a variety of different types of closure structures for use in conjunction with the present invention with suitable mating structure on the inner or outer surfaces of the upstanding arms 34 and 35. The closure top 10 is rotatably received between the spaced arms 34 and 35.

The illustrated closure top 10 has a generally cylindrical shaped base 67 with an upwardly extending break-off head 68. The base 67 includes a helically wound guide and advancement structure 71 that is sized, shaped and positioned so as to engage the guide and advancement structure 42 on the arms 34 and 35 to provide for rotating advancement of the closure structure 10 into the head 7 when rotated clockwise and, in particular, to cover the top or upwardly open portion of the U-shaped channel 38 to capture the rod 3, preferably without splaying of the arms 34 and 35. The base 67 further includes a lower point or projection 72. The projection 72 provides for increased friction against the rod 3. The closure structure 10 operably biases against the rod 3 at and near the projection or point 72 by advancement and applies pressure to the rod 3 under torquing, so that the rod 3 is urged downwardly against the shank domed top surface 29 that extends into the channel 38. Downward biasing of the shank top surface 29 operably produces a frictional engagement between the rod 3 and the surface 29 and also urges the retaining ring 8 toward the base 33 of the head 7, so as to frictionally seat the retaining ring spherical surface 65 fixedly against the partial internal spherical seating surface 49 of the head 7, also fixing the shank 6 and retaining ring 8 in a selected, rigid angular position relative to the head 7.

The closure structure break-off head 68 is secured to the base 67 at a neck 73 that is sized and shaped so as to break away at a preselected torque that is designed to properly seat the retaining ring 8 in the head 7. The break-off head 68 includes an external faceted surface 75, a central bore 77 and a pass-through slot 78 for receiving manipulating tools (not shown) and may also include grooves, or other apertures (not shown) for such purpose. The faceted surface 75 is sized and shaped to receive a conventional mating socket type head 87 of a driving/torquing tool 88 to rotate, drive and torque the closure structure 10.

The closure structure 10 also includes removal tool engagement structure which in the present embodiment is in the form of a hex-shaped and axially aligned aperture 81 disposed in the base 67, as shown in FIGS. 9 and 10. The hex aperture 81 is accessible after the break-off head 68 breaks away from the base 67. The aperture 81 is coaxial with the helically wound guide and advancement structure 71 and is designed to receive a hex tool, of an Allen wrench type, into the aperture 81 for rotating the closure structure base 67 subsequent to installation so as to provide for removal thereof, if necessary. Although a hex-shaped aperture 81 is shown in the drawings, the tool engagement structure may take a variety of tool-engaging forms and may include one or more apertures of various shapes, such as a pair of spaced apertures, a left-hand threaded bore, an easyout engageable step down bore, a hexalobular aperture (as sold under the TORX trademark), or other multi-lobular aperture or the like.

As shown in phantom in FIG. 2, prior to the assembly 1 being placed in use according to the invention, the retaining ring 8 is typically first inserted or top-loaded, into the head U-shaped channel 38, and then into the cavity 47 to dispose the retaining ring 8 within the inner surface 48 of the head 7. As shown in FIG. 2, the retaining ring outer edge defined by the top surface 58 slides along the inner surface 48 until the top surface 58 clears the shoulder 50. Then, the retaining ring 8 is rotated so as to be coaxial with the head 7 (the axis C aligned with the axis B), the top surface 58 facing the channel 38, and the surface 65 seated upon and in sliding engagement with the seating surface 49 as shown in solid lines in FIG. 2.

With reference to FIG. 3, the shank upper end 25 is then inserted or bottom-loaded into the head 7 through the bore 52 defined by the neck 54. The retaining ring 8, now disposed in the head 7 is coaxially aligned with the shank capture structure 21 at the upper end 25, so that the dome 29 passes through the bore 57 and the ring inner surface 60 is slidingly mated to the cylindrical surface 30 of the capture structure 21.

As shown in FIG. 3, the retaining ring 8 is preferably pushed upwardly into abutment with the shoulder 50 of the head 7 to provide ease in installment of the nut 9. The nut 9 is then downloaded through the channel 38 of the head 7, also as shown in FIG. 3, and then rotatingly mated with the helical thread 24 on the capture structure 21 of the shank 6, until the nut 9 abuts against the top surface 58 of the retaining ring 8. The assembly 1 is now assembled as shown in FIG. 4.

With reference to FIG. 5, the position of the nut 9 on the shank 6 is then fixed by inserting the set tool 62 between the upstanding arms 34 and 35 of the head 7 and pushing against the nut 9 with the set tool tip 63 at the weakened area 61, the tip 63 indenting the area 61 and also pressing against the threads 12 and 24, creating a deformed thread portion or area 64, locking the nut 9 to the capture structure 21, which in turn lodges the ring 8 in a fixed position with respect to the shank 6. The deformed thread portion 64 prevents counter-clockwise rotation of the nut 9 with respect to the capture structure 21, and thus prevents the nut 9 and the ring 8 from migrating up and off the shank upper end 25.

At this time the shank 6 is in slidable and rotatable engagement with the head 7, while the capture structure 21, the nut 9 and the retaining ring 8 cooperate to maintain the shank body 15 in rotational relation with the head 7. According to the embodiment of the invention shown in FIGS. 1-10, only the retaining ring 8 is in slidable engagement with the head spherical seating surface 49. Both the capture structure 21 and the threaded portion of the shank body 15 are in spaced relation with the head 7. The shank body 15 can be rotated through a substantial angular rotation relative to the head 7, both from side to side and from front to rear so as to substantially provide a universal or ball joint wherein the angle of rotation is only restricted by engagement of the neck 20 of the shank 6 with the neck 54 defining the bore 52 of the head. An example of such rotation is shown in FIGS. 9 and 10. The bevel 55 provides for a slight increase in the extent of angular rotation of the shank body 15 with respect to the head 7.

With reference to FIG. 7, the assembly 1 is then typically screwed into a bone, such as the vertebra 2 by rotation of the shank 6 using a suitable driving tool 90 that operably drives and rotates the shank 6 by engagement thereof with the faceted surfaces 13 of the nut 9 and also frictional engagement with the top surface 58 of the retaining ring 8.

The rod 3 is eventually positioned within the head U-shaped channel 38, as illustrated in FIG. 8, and the closure top 10 is then inserted into and advanced between the arms 34 and 35 so as to bias or push against the rod 3, the point 72 abrading and piercing the rod 3 as shown in FIG. 9.

The break-off head 68 of the closure top 10 is torqued utilizing the driving/torquing tool 88 disposed about the external faceted surface 75, to a preselected torque, for example 90 to 130 inch pounds, to further urge the rod 3 downwardly. The shank dome 29, because it is radiused and sized to extend upwardly into the U-shaped channel 38, is engaged by the rod 3 and pushed downwardly when the closure top 10 pushes downwardly on the rod 3, also as shown in FIG. 9. The downward pressure on the shank 6 in turn urges the retaining ring 8 downwardly which causes both a downward and outward thrust of the retaining ring 8.

FIG. 10 illustrates the polyaxial bone screw assembly 1, the rod 3 and the closure top base 67 positioned in the vertebra 215 with the break-off head 68 being removed by the torquing tool 88. The axis A of the bone shank 15 is illustrated as not being coaxial with the axis B of the head 7 and the shank body 15 is fixed in this angular locked configuration. Other angular configurations can be achieved, as required during installation surgery due to positioning of the rod 3 or the like.

If removal of the assembly 1 from the vertebra 2 is necessary, the assembly 1 can be disassembled by mating an allen-wrench tool (not shown) with the closure top bore 81 to rotate the base 67 in a counter-clockwise direction between and out of the arms 34 and 35. The driving tool 90 may then be inserted on the nut 9 and rotated in a counter-clockwise direction. Because of the deformation area 64 of the threads 12 and/or 24, the nut 9 does not disassemble from the shank 6 when the nut is rotated counter-clockwise. Thus, the counter-clockwise rotation of the nut 9 also rotates the shank body 15 along and out of the vertebra 2, removing the assembly 1 as a single unit out of the vertebra 2.

It is to be understood that while certain forms of the present invention have been illustrated and described herein, it is not to be limited to the specific forms or arrangement of parts described and shown.

What is claimed and desired to be secured by Letters Patent is as follows:

1. A polyaxial bone screw assembly comprising:
   (a) a shank having a body for fixation to a bone and a capture structure extending from the body, the capture structure having an outer surface with a first helically wound guide and advancement structure and a smooth surface disposed between the first guide and advancement structure and the body;
   (b) a head having a top portion and a base, the head top portion defining an open channel adapted to receive a rod implant, the base having a seating surface partially defining a cavity, the channel communicating with the cavity, the cavity communicating with an exterior of the base through an opening sized and shaped to receive the capture structure therethrough; and
   (c) a retaining ring having an external surface and an internal surface defining a central bore configured to slidably mate with the smooth surface of the capture structure, the retaining ring external surface configured to be in slidable mating engagement with the seating surface of the head so as to enable selective angular positioning of the shank body with respect to the head; and
   (d) a fastener having an internal surface with a second helically wound guide and advancement structure thereon, the first helically wound guide and advancement structure configured to rotatably mate with the second helically wound guide and advancement structure to secure the fastener and the retaining ring to the capture structure within the head cavity, the fastener having structure thereon adapted to mate with a tool for operably implanting the shank in a bone of a patient, when the shank, retainer ring, fastener and head are assembled, the shank capture structure extending into the channel so as to engage a rod placed in the channel under pressure and thereby lock the shank in a desired angular configuration with respect to the head.

2. The assembly of claim 1 wherein the fastener is a nut having a faceted outer surface with at least one facet of the nut having a weakened area compressible by an outside pressing force directed at the weakened area, and when attached to the capture structure at least one of the first and second guide and advancement structures being deformable by the outside force pressing on the weakened area, interlocking the first and second guide and advancement structures.

3. The assembly of claim 1 wherein the shank capture structure includes an annular seating surface and the retaining ring has a top and a bottom, the retaining ring bottom abutting the annular seating surface when the retaining ring is received on the capture structure and the fastener is rotated onto the capture structure with the first and second guide and advancement structures mated and the fastener pressing against the retaining ring top.

4. The assembly of claim 1 wherein the head cavity is partially defined by an upper shoulder portion having a planar surface disposed perpendicular to an axis of rotation of the head.

5. The assembly of claim 4 wherein the upper shoulder portion includes first and second coplanar surfaces.

6. The assembly of claim 1 wherein:
  (a) the head seating surface that is located to be in slidable mating engagement with the retaining ring external surface is substantially spherical; and
  (b) the retaining ring external surface that is in slidable mating engagement with the head seating surface is substantially spherical.

7. The assembly of claim 1 wherein the retaining ring has a planar top surface adjacent the fastener and the fastener is a nut having a faceted outer surface, the planar top surface and faceted outer surface cooperating to provide non-slip engagement by a tool for driving the shank body into bone.

8. The assembly of claim 1 wherein the first helically wound guide and advancement structure is a raised helical rib.

9. The assembly of claim 1 wherein the second helically wound guide and advancement structure is a raised helical rib.

10. The assembly of claim 1 wherein the retaining ring is sized and shaped to be loadable into the head through the open channel and the shank is sized and shape to be loadable into the head through the base opening.

11. The assembly of claim 1 further comprising a closure structure insertable into the head, the closure structure for operably urging the shank in a direction to frictionally lock the position of the retaining ring external surface relative to the head seating surface, thereby locking the shank body in a selected angle with respect to the head.

12. The assembly of claim 11 wherein:
  (a) the head has upstanding spaced arms defining the open channel, the arms having guide and advancement structures on an inside surface thereof; and
  (b) the closure structure is sized and shaped to be positionable between the arms for closing the channel, the closure structure having a closure guide and advancement structure for rotatably mating with the guide and advancement structures on the arms, biasing the closure structure upon advancement rotation against a rod disposed in the channel.

13. The assembly of claim 11 wherein the capture structure end has a dome sized and shaped to extend into the channel for engagement with a rod when received in the head and wherein the closure structure is adapted to operably urge the rod against the dome upon the closure structure being positioned in the head.

14. In a polyaxial bone screw assembly for surgical implantation and including a shank having an upper end and a threaded body for inserting into a bone and a head having an outward opening channel adapted to receive a rod within the channel, the head having a shank receiving opening, the improvement comprising:
  (a) a capture structure disposed on the shank upper end sized and configured to be uploaded through the shank receiving opening, the capture structure having an outer surface with a first helically wound guide and advancement structure and a smooth cylindrical surface disposed adjacent the first helically wound advancement structure;
  (b) a retaining ring having an external surface and a smooth inner cylindrical surface defining a bore, the smooth inner cylindrical surface configured to slidably mate with the smooth cylindrical surface of the capture structure; and
  (c) a nut having a faceted external surface and an internal surface with a second helically wound guide and advancement structure, after assembly the nut being positioned between the channel and the retaining ring and operably receiving a tool to drive the shank into a patient's bone, the first helically wound guide and advancement structure configured to rotatably mate with the second helically wound guide and advancement structure to secure the retaining ring to the capture structure within the head, when assembled and in a non-locked configuration, the retaining ring external surface enabling selective angular positioning of the shank with respect to the head, the shank capture structure extending into the channel after assembly to engage the rod and, under pressure from the rod, the retaining ring is urged against the head and locked in a selected angular configuration with respect to the head.

15. The improvement of claim 14 wherein:
  (a) the head has an inner substantially spherical seating surface partially defining a cavity, the cavity communicating with both the channel and the shank receiving opening; and
  (b) the retaining ring external surface is substantially spherical and in slidable mating engagement with the head seating surface.

16. The improvement of claim 14 wherein at least one facet of the nut has a weakened area compressible by an outside pressing force directed at the weakened area, and when attached to the capture structure at least one of the first and second guide and advancement structures being deformable by the outside force pressing on the weakened area, interlocking the first and second guide and advancement structures.

17. The improvement of claim 14 wherein the shank capture structure includes an annular seating surface and the retaining ring has a top and a bottom, the retaining ring bottom abutting the annular seating surface when the retaining ring is received on the capture structure and the nut is rotated onto the capture structure with the first and second guide and advancement structures mated and the nut pressing against the retaining ring top.

18. The improvement of claim 14 wherein the first helically wound guide and advancement structure is a raised helical rib.

19. The improvement of claim 14 wherein the second helically wound guide and advancement structure is a raised helical rib.

20. A polyaxial bone screw assembly comprising:
  (a) a shank having a body for fixation to a bone and a capture structure extending from the body, the capture structure having an annular seating surface and a cylindrical surface with a first helically wound guide and advancement structure and a smooth surface disposed between the first guide and advancement structure and the annular seating surface;

(b) a head having a top portion and a base, the head top portion defining an open channel for receiving a rod, the base having a substantially hemispherical seating surface partially defining a cavity, the channel communicating with the cavity, the cavity communicating with an exterior of the base through an opening sized and shaped to receive the capture structure therethrough;

(c) a retaining ring having a substantially hemispherical external surface configured to slidingly mate with the substantially hemispherical seating surface of the head, and an internal surface defining a central bore configured to slidably mate with the smooth surface of the capture structure, the retaining ring external surface configured to be in slidable mating engagement with the seating surface of the head so as to enable selective angular positioning of the shank body with respect to the head; and (d) a nut that after assembly is located between the retaining ring and the channel and having a faceted outer surface and an internal surface having a second helically wound guide and advancement structure thereon, the first helically wound guide and advancement structure configured to rotatably mate with the second helically wound guide and advancement structure to frictionally fix the retaining ring between the nut and the annular seating surface of the capture structure, at least one facet of the nut having a weakened area compressible by an outside pressing force directed at the weakened area, at least one of the first and second guide and advancement structures being deformable by the outside force, thereby interlocking the first and second guide and advancement structures and locking the retaining ring between the nut and the annular seating surface within the head, the nut being sized, shaped and positioned to receive a tool for driving the shank into a bone of a patient and removing the shank from the bone, the shank capture structure extending into the channel after assembly and receiving pressure from a rod in the channel so as to bias the shank and retaining ring against the head and thereby lock the angular configuration of the shank relative to the head.

21. The assembly of claim 20 wherein the head cavity is partially defined by an upper shoulder portion having a planar surface disposed perpendicular to an axis of rotation of the head.

22. The assembly of claim 20 wherein the upper shoulder portion includes first and second coplanar surfaces.

23. The assembly of claim 20 wherein the retaining ring has a planar top surface adjacent the nut faceted outer surface, the planar top surface and faceted outer surface cooperating to provide non-slip engagement by a tool for driving the shank body into bone.

24. The assembly of claim 20 further comprising a closure structure insertable into the head, the closure structure for operably urging the shank in a direction to frictionally lock the position of the retaining ring external surface relative to the head seating surface, thereby locking the shank body in a selected angle with respect to the head.

25. The assembly of claim 24 wherein:

(a) the head has upstanding spaced arms defining the open channel, the arms having guide and advancement structures on an inside surface thereof; and (b) the closure structure is sized and shaped to be positionable between the arms for closing the channel, the closure structure having a closure guide and advancement structure for rotatably mating with the guide and advancement structures on the arms, biasing the closure structure upon advancement rotation against a rod disposed in the channel.

26. The assembly of claim 24 wherein the capture structure end has a dome sized and shaped to extend into the channel for engagement with a rod when received in the head and wherein the closure structure is adapted to operably urge the rod against the dome upon the closure structure being positioned in the head.

27. A polyaxial bone screw assembly method comprising:

(a) inserting a retaining ring through a channel and into a cavity of a head, the head channel opening outwardly and adapted to receive a rod within the channel, the head cavity being disposed between and communicating with both the channel and a shank receiving opening, the retaining ring having an inner cylindrical surface defining a bore;

(b) inserting a capture structure of a bone screw shank through the shank receiving opening of the head and into the cavity thereof, the capture structure being integral with an elongate threaded shank body and having an outer surface with a first helically wound guide and advancement structure thereon adjacent to a smooth cylindrical surface, the shank, after assembly with the head, extending into the channel;

(c) attaching the capture structure to the retaining ring within the cavity by inserting the capture structure through the bore until the inner cylindrical surface of the retaining ring is in sliding engagement with the smooth cylindrical surface of the capture structure, and inserting a nut having a second helically wound guide and advancement structure onto the capture structure and rotating the nut, mating the first and second helically wound guide and advancement structures;

(d) subsequent to step (c) utilizing a tool applied to the nut to drive the shank into a bone, and (e) after the shank is driven into a bone, placing a rod in the channel and applying pressure to the rod to engage the shank and lock the shank in a fixed angular configuration with respect to the head.

28. The method of claim 27 further comprising:

(d) driving the shank body into bone by rotating the shank body with a tool engaged with the nut.

29. The method of claim 28 further comprising:

(e) subsequently inserting a rod into the channel; and (f) biasing the rod against the capture structure by inserting a closure structure into the channel.

30. A method of assembling a polyaxial bone screw comprising the steps of:

(a) providing a bone screw shank, head, retaining ring and nut;

(b) providing the shank with an upper threaded capture structure;

(c) providing the retaining ring with an inner cylindrical surface defining a bore;

(d) providing the head with a central cavity, a rod receiving channel and a shank receiving bore connecting the cavity with an underside of the head;

(e) loading the retaining ring into the cavity;

(f) uploading the shank capture structure into the cavity through the shank receiving bore and the retaining ring bore;

(g) screwing the nut onto the shank capture structure while within the head;
(h) driving the shank into a bone by utilizing a tool placed on the nut;
(i) extending the shank into the channel; and
(j) placing a rod in the channel to engage the shank so as to bias the shank and retainer against the head and lock the shank in a fixed angular configuration with respect to the head.

31. The method according to claim 30 including the steps of:

(a) providing the head with an upwardly open channel that communicates with the cavity; and
(b) downloading the retaining ring and the nut through the channel into the cavity.

\* \* \* \* \*